United States Patent
Nishino et al.

(10) Patent No.: US 8,247,787 B2
(45) Date of Patent: Aug. 21, 2012

(54) RADIOGRAPHIC IMAGE CAPTURING SYSTEM

(75) Inventors: Naoyuki Nishino, Minami-ashigara (JP);
Keiji Tsubota, Minami-ashigara (JP);
Yasunori Ohta, Yokohama (JP); Yutaka Yoshida, Fuchu (JP); Masato Hattori, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 343 days.

(21) Appl. No.: 12/654,102

(22) Filed: Dec. 10, 2009

(65) Prior Publication Data

US 2010/0148076 A1  Jun. 17, 2010

(30) Foreign Application Priority Data

Dec. 11, 2008  (JP) ................................. 2008-315622
Nov. 30, 2009  (JP) ................................. 2009-271500

(51) Int. Cl.
*G01T 1/17* (2006.01)
(52) U.S. Cl. ...................................................... 250/582
(58) Field of Classification Search ................... 250/582
See application file for complete search history.

(56) References Cited

U.S. PATENT DOCUMENTS

| | | | | |
|---|---|---|---|---|
| 7,250,608 B2 * | 7/2007 | Ozeki | ....................... | 250/370.08 |
| 7,542,542 B2 * | 6/2009 | Li | ................................... | 378/15 |
| 2002/0060302 A1 * | 5/2002 | Aonuma | ....................... | 250/583 |
| 2007/0253534 A1 * | 11/2007 | Abe | ............................... | 378/116 |
| 2009/0154648 A1 * | 6/2009 | Watanabe | ..................... | 378/116 |

FOREIGN PATENT DOCUMENTS

| | | |
|---|---|---|
| JP | 2003-024317 | 1/2003 |
| JP | 2008-142314 | 6/2008 |
| JP | 2008-167841 | 7/2008 |
| JP | 2008258044 A * | 10/2008 |

* cited by examiner

*Primary Examiner* — David Porta
*Assistant Examiner* — Hugh H Maupin
(74) *Attorney, Agent, or Firm* — Jean C. Edwards, Esq.; Edwards Neils PLLC

(57) ABSTRACT

When a first image capturing apparatus installed in an image capturing room is selected and a power supply switch of a radiation converter used in the first image capturing apparatus is turned on, a controller generates an image capturing apparatus identification signal for specifying the image capturing apparatus, and sends the identification signal together with ID information of the selected image capturing apparatus stored in an ID memory to a console in the image capturing room via a transceiver by wireless communications. The console reads image capturing conditions for the selected image capturing apparatus from an image capturing condition storage unit, and supplies the conditions to a radiation generator for recording a radiographic image in the radiation converter. The radiation generator controls a radiation source according to the supplied conditions to emit radiation for recording a desired radiographic image on a radiation conversion panel of the radiation converter.

14 Claims, 7 Drawing Sheets

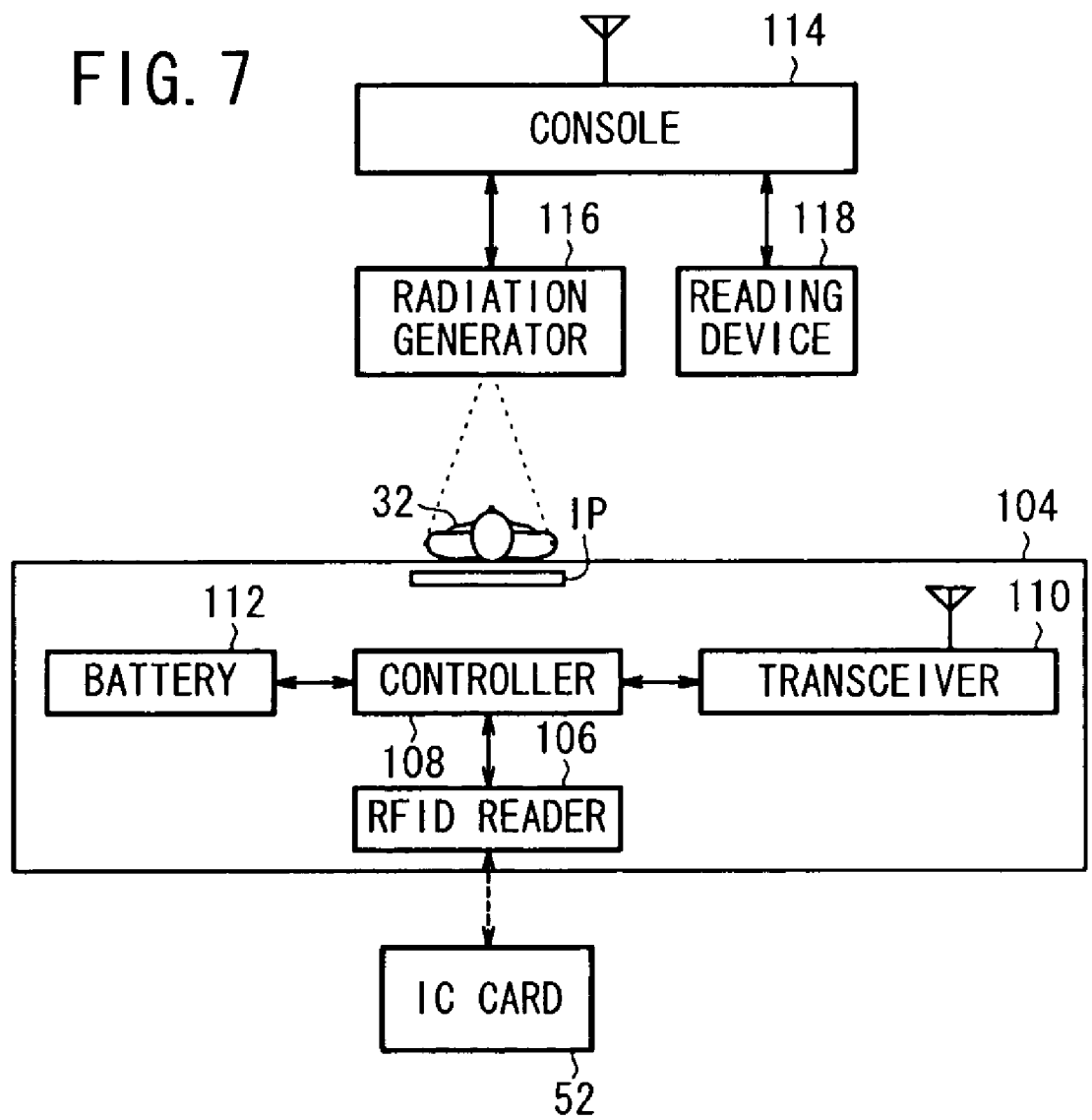

RADIOGRAPHIC IMAGE CAPTURING SYSTEM

CROSS-REFERENCE TO RELATED APPLICATION

This application is based upon and claims the benefit of priority from Patent Applications No. 2008-315622 filed on Dec. 11, 2008 and No. 2009-271500 filed on Nov. 30, 2009, in the Japan Patent Office, of which the contents are incorporated herein by reference.

BACKGROUND OF THE INVENTION

1. Field of the Invention

The present invention relates to a radiographic image capturing system for acquiring a radiographic image of a subject by controlling a selected image capturing unit with a processor that is associated with the selected image capturing unit.

2. Description of the Related Art

In the medical field, there have widely been used image capturing apparatus which apply radiation to a subject and guide the radiation that has passed through the subject to a radiation conversion panel, which captures a radiographic image from the radiation.

One known radiation conversion panel is a stimulable phosphor panel which stores a radiation energy representative of a radiographic image in a phosphor. When the stimulable phosphor panel is irradiated with stimulating light, the phosphor emits stimulated light representative of the stored radiographic image. The stimulable phosphor panel with the radiographic image recorded therein is supplied to a reading apparatus which reads the stored radiographic image as a visible radiographic image.

In sites of medical practice such as operating rooms or the like, it is necessary to read recorded radiographic image information immediately from a radiation conversion panel for the purpose of quickly and appropriately treating the patient. As a radiation conversion panel which meets such a requirement, there has been developed a radiation converter having a solid-state imaging device for converting a radiation directly into an electric signal or converting a radiation into visible light with a scintillator and then converting the visible light into an electric signal to read a detected radiographic image.

There are available in the art various image capturing apparatus of different specifications for capturing radiographic images using such radiation conversion panels depending on the conditions of patients as subjects to be imaged and their body regions to be imaged. Those different image capturing apparatus include an image capturing apparatus for capturing a radiographic image of the chest of a patient while the patient is standing up, an image capturing apparatus for capturing a radiographic image of the abdominal region of a patient while the patient is lying on a bed, and an image capturing apparatus for capturing a radiographic image of a patient while the patient is sitting in a wheelchair. Some body regions of patients are imaged using a stimulable phosphor panel or a radiation converter which is stored in a cassette.

In the radiological departments of large hospitals, image capturing apparatus or image capturing units comprising cassettes are installed in respective image capturing rooms. Each of the image capturing rooms houses therein a console (processor) for setting, in a radiation source, image capturing conditions corresponding to the radiation conversion panel placed in the image capturing room, e.g., a tube voltage, a tube current, an irradiation time, etc. depending on the sensitivity of the radiation conversion panel and the body region to be imaged of the patient, and processing and displaying a captured radiographic image. The console receives an image capturing order, which has been made by a doctor using an RIS (Radiology Information System), through an in-house network. A radiological technician operates the console to confirm the details of the image capturing order, selects an image capturing unit specified by the image capturing order, and performs an image capturing process on the selected image capturing unit. The image capturing order includes patient information representing the name, age, etc. of the patient and also information representing the image capturing unit designated by the doctor, an image capturing method, etc.

The image capturing unit and the console need to be properly related to each other because the image capturing unit has to acquire image capturing conditions for capturing appropriate radiographic images from the console. Furthermore, in order for the radiological technician to confirm radiographic images with increased efficiency and to prevent patients from being mistaken, it is necessary to supply radiographic images captured by the image capturing unit to the console, so that the console can process the radiographic images in accurate association with the patient information.

According to the related art disclosed in Japanese Laid-Open Patent Publication No. 2008-142314 and Japanese Laid-Open Patent Publication No. 2008-167841, a plurality of consoles and a plurality of radiation converters (FPD: Flat Panel Detector) are connected to each other through a wireless access point (see Paragraph [0038], FIG. 3 of the former publication and Paragraph [0033], FIG. 3 of the latter publication), and each console or each FPD is prevented from accepting a plurality of image capturing orders redundantly, so that the consoles and the FPD are correctly associated with each other for thereby preventing patients from being mistaken.

According to the related art disclosed in Japanese Laid-Open Patent Publication No. 2003-024317, one console (controller) and a plurality of image capturing apparatus are connected by connecting cables (see Paragraph [0004], FIG. 5 of the publication). One of the image capturing apparatus is selected, and a radiographic image captured by the selected image capturing apparatus is sent to the console connected thereto by the connecting cable and processed by the console.

In an image capturing room of the radiological department of a hospital, a radiological technician may be unable to select an image capturing unit which a doctor has specified in an image capturing order. For example, when the doctor specifies an upstanding image capturing apparatus to capture radiographic images of a patient in an image capturing order, the patient may not take an upstanding posture due to physical limitations. In such a case, the radiological technician has to change to an imaging process which uses either an image capturing apparatus for capturing radiographic images of a patient while lying on a bed or a cassette housing an FPD or a stimulable phosphor panel therein.

When the radiological technician changes the specified image capturing unit to another image capturing apparatus or a cassette, if the console fails to recognize the change and make proper settings about the association of the console and the changed image capturing apparatus or cassette, then inappropriate image capturing conditions may be set in the changed image capturing apparatus or cassette, possibly resulting in a failure to acquire the radiographic images of the patient.

Furthermore, the radiological technician has to select the size of a cassette required to capture a radiographic image and a cassette which has been charged that is capable of capturing a radiographic image, and also has to change the information about the changed cassette through the console. The invention disclosed in Japanese Laid-Open Patent Publication No. 2008-142314 only serves to prevent each console or each FPD from accepting a plurality of image capturing orders redundantly, and does not deal with changes in the association between the consoles and the FPDs. Consequently, the radiological technician needs to take the trouble of separately changing the association. According to the invention Japanese Laid-Open Patent Publication No. 2003-024317, since the relationship between the image capturing apparatus and the console is fixed by the connecting cables, changes in the connections between the image capturing apparatus and the console cannot be dealt with.

SUMMARY OF THE INVENTION

It is an object of the present invention to provide a radiographic image capturing system which is capable of accurately and easily setting the association between an image capturing unit for capturing a radiographic image and a processor for controlling the image capturing unit according to image capturing conditions, for thereby acquiring appropriate radiographic images at all times.

According to the present invention, a radiographic image capturing system includes a plurality of image capturing units for capturing a radiographic image of a subject, a processor for supplying image capturing conditions to a selected one of the image capturing units and processing the radiographic image captured by the selected one of the image capturing units, an identification signal generating unit for generating an identification signal which identifies the selected one of the image capturing units, and an associating unit for associating the selected one of the image capturing units with the processor according to the identification signal. The image capturing conditions are supplied from the associated processor to the selected one of the image capturing units that has been selected by a unit except the processor, and the radiographic image is supplied from the selected one of the image capturing units to the associated processor.

With the above arrangement, a unit except the processor, e.g., an image capturing unit selected by the radiological technician who handles the image capturing units, is identified, and the corresponding processor is associated with the selected image capturing unit according to an identification signal of the image capturing unit. The image capturing unit and the processor are thus automatically associated with each other accurately and easily. As a result, the processor can supply appropriate image capturing conditions to the selected image capturing unit, and acquire an appropriate radiographic image from the selected image capturing unit.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 7 is a block diagram of a radiographic image capturing system according to yet another embodiment of the present invention.

DESCRIPTION OF THE PREFERRED EMBODIMENTS

Figure 1:
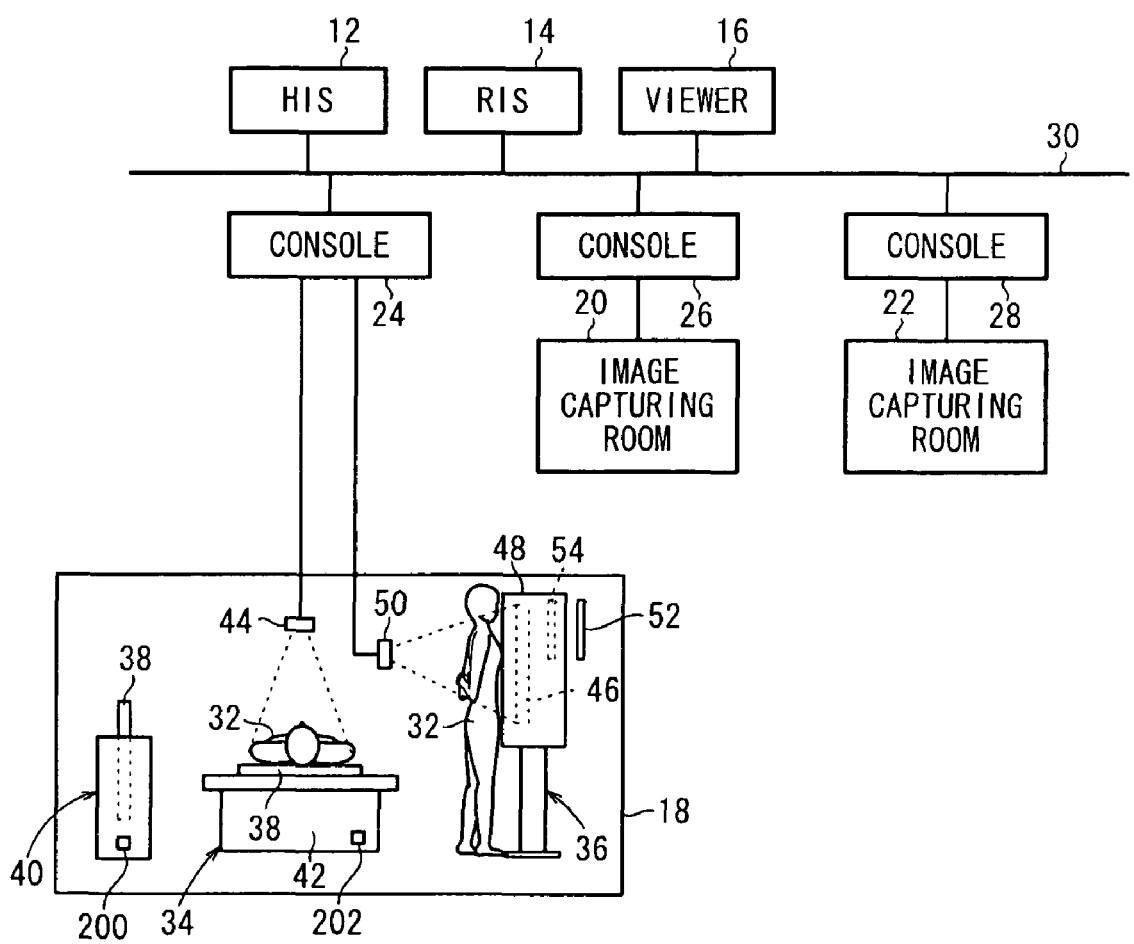
FIG. 1 is a block diagram of a radiographic image capturing system according to an embodiment of the present invention.

FIG. 1 shows in block form a radiographic image capturing system 10 according to an embodiment of the present invention.

As shown in FIG. 1, the radiographic image capturing system 10 comprises a hospital information system (HIS) 12 for managing medical information in a hospital, a radiology information system (RIS) 14 for managing a process of capturing radiographic images in the radiological department of the hospital under the management of the HIS 12, a viewer 16 for allowing a doctor to interpret captured radiographic images for the purpose of diagnosis, and consoles (processors) 24, 26, 28 installed in respective rooms adjacent to a plurality of image capturing rooms 18, 20, 22 in the radiological department. The consoles 24, 26, 28 serve to manage and control various image capturing apparatus having different specifications and image capturing units including radiation converters, radiation conversion panels, stimulable phosphor panels, etc. The HIS 12, the RIS 14, the viewer 16, and the consoles 24, 26, 28 are interconnected by an in-house network 30 in the hospital.

The image capturing room 18 houses therein a first image capturing apparatus (image capturing unit) 34 for capturing radiographic images of a subject 32, typically a patient, while the subject 32 is lying, a second image capturing apparatus (image capturing unit) 36 for capturing radiographic images of a subject 32 while the subject 32 is standing, and a cradle 40 for charging a radiation converter 38 for use in the first image capturing apparatus 34. The other image capturing rooms 20, 22 also house desired image capturing units therein.

The first image capturing apparatus 34 comprises an image capturing base 42 and a radiation generator 44 for applying radiation through the subject 32 to the radiation converter 38 which is placed on the image capturing base 42. The second image capturing apparatus 36 comprises an image capturing base 48 which incorporates a radiation conversion panel 46 therein and a radiation generator 50 for applying radiation through the subject 32 to the radiation conversion panel 46. The image capturing base 48 includes an RFID reader (information reading unit) 54 for reading an IC card 52 which stores ID information of the subject 32 recorded therein.

Figure 2:
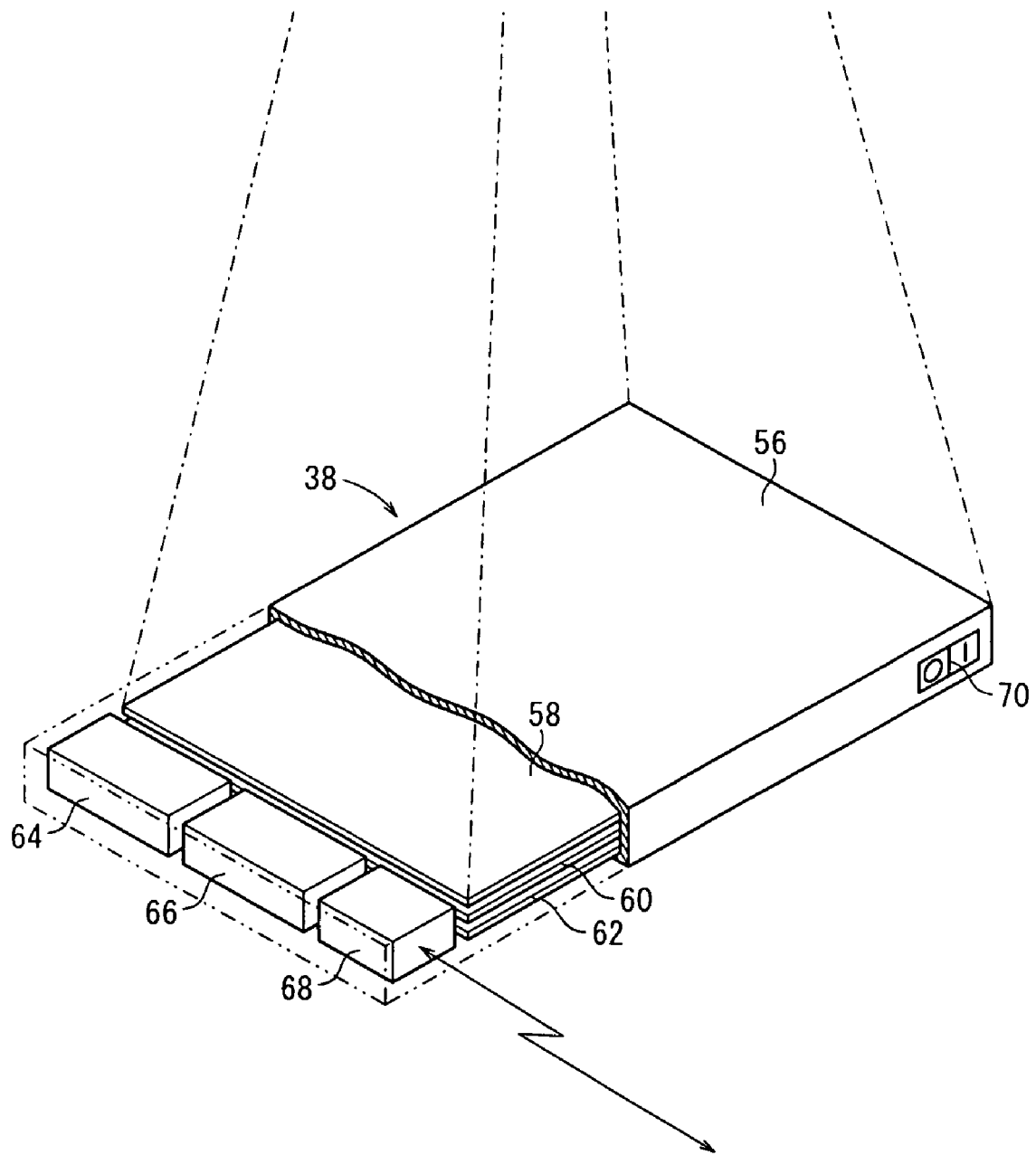
FIG. 2 is a perspective view, partly broken away, of a radiation converter for use in the radiographic image capturing system shown in FIG. 1.

FIG. 2 shows in perspective internal structural details of the radiation converter 38 used in the first image capturing apparatus 34. As shown in FIG. 2, the radiation converter 38 has a casing 56 made of a material permeable to the radiation. The casing 56 houses therein a grid 58 for removing scattered rays of the radiation from the subject 32, a radiation conversion panel 60 for detecting the radiation that has passed through the subject 32 and converting the radiation into electric charge information, and a lead plate 62 for absorbing back scattered rays of the radiation, which are successively arranged in the order named from a surface of the casing 56 which is irradiated with the radiation. The irradiated surface of the casing 56 may be constructed as the grid 58.

The radiation conversion panel 60, which is a so-called flat panel detector (FPD), may be of a structure including a matrix of thin film transistors (TFTs) and a photoelectric conversion layer which is deposited over the matrix of TFTs and which is made of amorphous selenium (a-Se) or the like for detecting radiation and generating electric charges depending on the detected radiation, so that the radiation conversion panel 60 can generate an image signal representing the electric charges generated by the TFTs.

The casing 56 also houses therein a battery 64 as a power supply of the radiation converter 38, a controller 66 for energizing the radiation converter 38 with electric power supplied from the battery 64, and a transceiver (wireless transceiver unit) 68 for sending a signal representing a radiographic image of the subject 32 which has been converted by the radiation converter 38 to the console 24 that is connected to the image capturing room 18. The casing 56 has a power supply switch (operating unit) 70 on a side wall thereof for activating the radiation converter 38. The power supply switch 70 also functions as an identification signal generating unit for generating an identification signal for identifying the radiation converter 38 which has been selected by the radiological technician.

Figure 3:
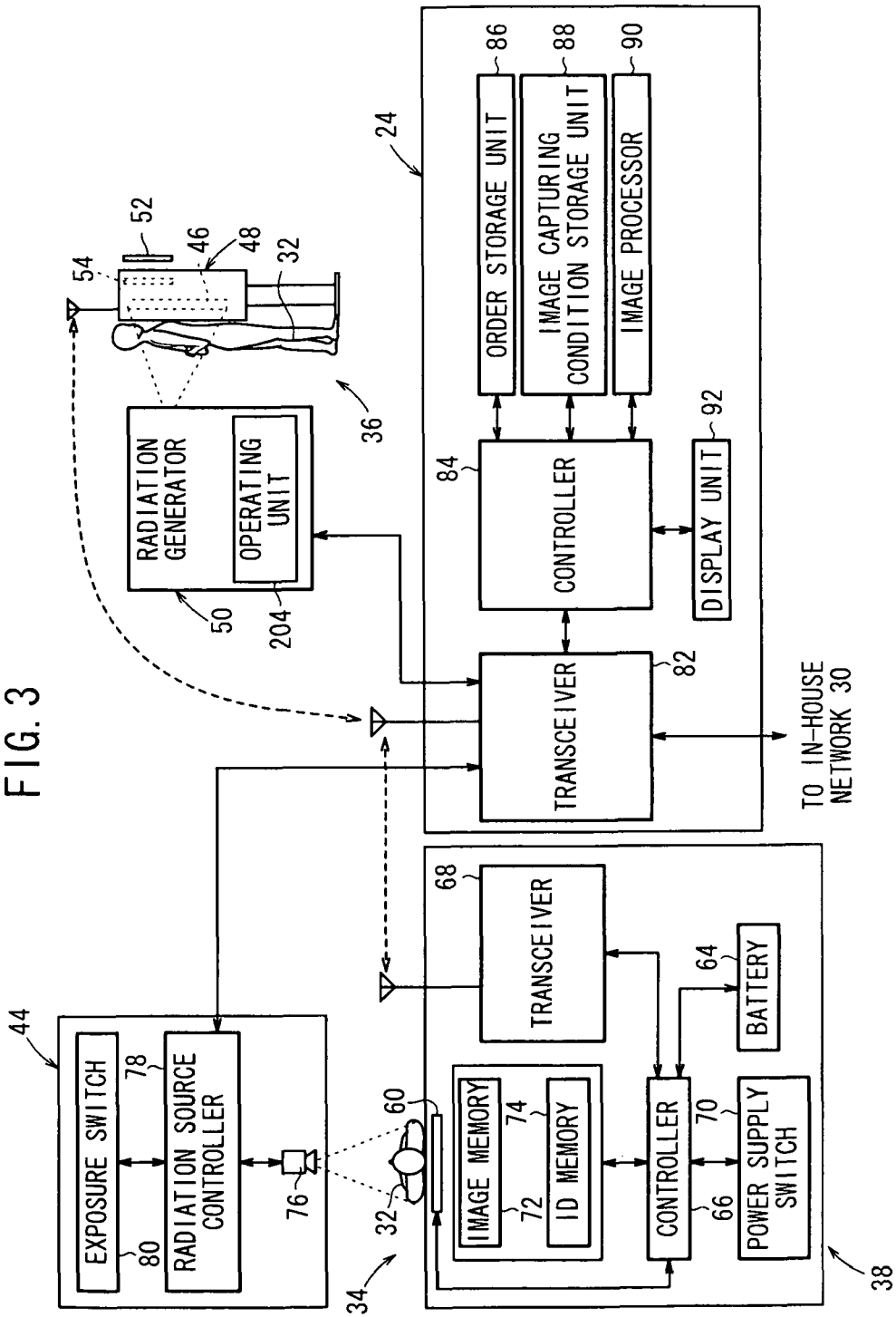
FIG. 3 is a block diagram of a portion of the radiographic image capturing system shown in FIG. 1.

FIG. 3 shows in block form the console 24 and the first and second image capturing apparatus 34, 36 housed in the image capturing room 18 that is managed by the console 24. The consoles 26, 28 and the image capturing rooms 20, 22 are also similarly constructed.

The radiation converter 38 of the first image capturing apparatus 34 includes an image memory 72 for storing a radiographic image converted by the radiation conversion panel 60 as an image signal, and an ID memory 74 for storing ID information which identifies the radiation converter 38. The transceiver 68 of the radiation converter 38 sends the radiographic image stored in the image memory 72 to the console 24 by way of wireless communications. The radiation generator 44 of the first image capturing apparatus 34 comprises a radiation source 76 for emitting radiation, a radiation source controller 78 for controlling the radiation source 76, and an exposure switch (operating unit) 80.

The image capturing base 48 of the second image capturing apparatus 36 sends a radiographic image converted by the radiation conversion panel 46 to the console 24 by way of wireless communications. The radiation generator 50 is of a structure similar to the radiation generator 44 of the first image capturing apparatus 34.

The console 24 includes a transceiver 82 which sends and receives signals to and from the HIS 12, the RIS 14, the viewer 16, and the other consoles 26, 28 via the in-house network 30, and which also sends and receives signals including identification signals, to and from the first and second image capturing apparatus 34, 36 in the image capturing room 18. The console 24 is controlled by a controller 84. The controller 84 is connected to an order storage unit (order holding unit) 86 for storing an image capturing order acquired from the RIS 14, an image capturing condition storage unit (image capturing condition holding unit) 88 for storing image capturing conditions for the first and second image capturing apparatus 34, 36 which have been acquired from the RIS 14 or set on the console 24 by the radiological technician, an image processor 90 for processing a radiographic image acquired from the first image capturing apparatus 34 or the second image capturing apparatus 36, and a display unit 92 for displaying the processed radiographic image. The controller 84 also functions as an associating unit for associating, as associated devices, the console 24 with the first image capturing apparatus 34 or the second image capturing apparatus 36 which has been selected by the radiological technician as a unit in the image capturing room 18, 20, or 22, other than (except) the consoles 24, 26, 28 of the radiographic image capturing system 10, according to the ID information which specifies the first image capturing apparatus 34 or the second image capturing apparatus 36.

Figure 4:
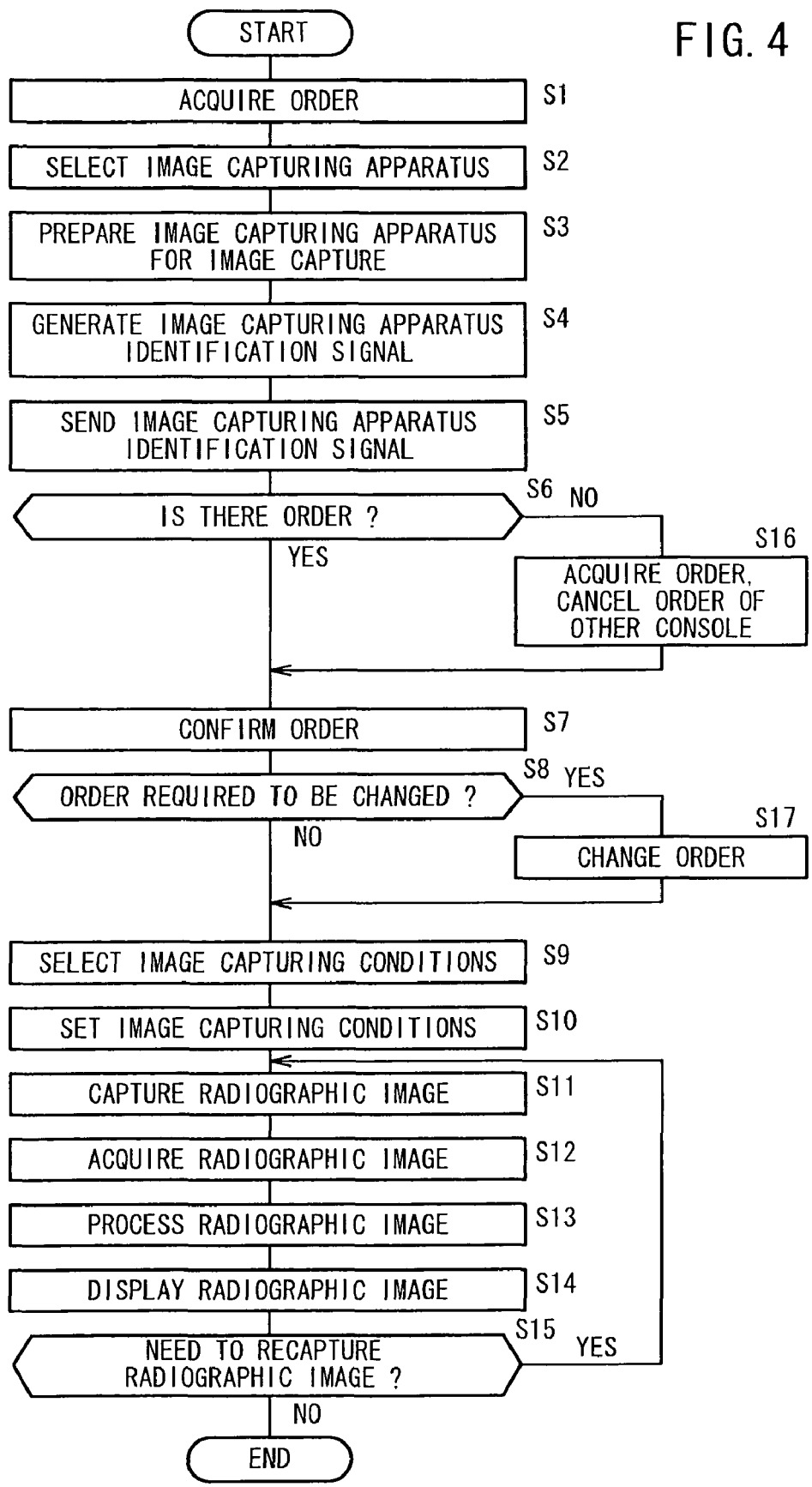
FIG. 4 is a flowchart of an operation sequence of the radiographic image capturing system shown in FIG. 1.

The radiographic image capturing system 10 according to the present embodiment is basically constructed as described above, and operation of the radiographic image capturing system 10, mainly the console 24 and the image capturing room 18, will be described below with reference to a flowchart shown in FIG. 4.

First, the transceiver 82 of the console 24 acquires an image capturing order from the RIS 14 via the in-house network 30 in step S1. The image capturing order is generated by the doctor using the RIS 14. The image capturing order includes patient information including the name, age, gender, etc. about the patient, i.e., the subject 32, and an image capturing apparatus to be used for capturing a radiographic image of the subject 32, a body region of the subject 32 which is to be imaged, an image capturing method, and image capturing conditions. The image capturing conditions are conditions for determining a dose of radiation to be applied to the subject 32, e.g., a tube voltage and a tube current of the radiation source 76, an irradiation time, etc.

Then, the radiological technician operates the console 24 to display the acquired image capturing order on the display unit 92 and select the image capturing apparatus to be used for capturing a radiographic image of the subject 32 based on the image capturing order in step S2. Then, the radiological technician takes an action to prepare for the capture of a radiographic image in step S3.

Specifically, if the first image capturing apparatus 34 for capturing a radiographic image of the subject 32 while the subject 32 is lying on the image capturing base 42 is selected, then the radiological technician places the radiation converter 38 whose battery 64 has been charged by the cradle 40 on the image capturing base 42, and positions the subject 32 on the radiation converter 38. If the second image capturing apparatus 36 for capturing a radiographic image of the subject 32 while the subject 32 is in an upstanding posture, then the radiological technician positions the subject 32 on the image capturing base 48.

If the first image capturing apparatus 34 is selected by the radiological technician, then the radiological technician thereafter turns on the power supply switch 70 of the radiation converter 38, preparing the radiation converter 38 for the capture of a radiographic image of the subject 32. Specifically, when the power supply switch 70 is turned on, the controller 66 of the radiation converter 38 generates an image capturing apparatus identification signal indicating that the radiation converter 38 is selected as an image capturing unit in step S4, and sends the ID information for specifying the radiation converter 38, which is stored in the ID memory 74, from the transceiver 68 to the console 24 in the first image capturing room 18 by way of wireless communications in step S5. Since the power supply switch 70 has been turned on by the radiological technician, the selected radiation converter 38 is guaranteed to be prepared for the capture of a radiographic image of the subject 32. Consequently, the image capturing unit is free from such a failure that it is not activated and is unable to capturing a radiographic image of the subject 32 when an image capturing unit is selected on the console 24 and image capturing conditions are sent from the console 24 to the selected image capturing unit.

If the second image capturing apparatus 36 is selected by the radiological technician, then the radiological technician thereafter bring the IC card 52 which holds the patient information, closely to the RFID reader 54 housed in the image capturing base 48. The RFID reader 54 reads the ID information which specifies the second image capturing apparatus 36, and the read ID information is sent as an image capturing apparatus identification signal to the console 24 in the image capturing room 18.

The controller 84 of the console 24 confirms whether the order storage unit 86 stores an image capturing order for the subject 32 or not in step S6. If the order storage unit 86 stores an image capturing order for the subject 32 ("YES" in step S6), then the controller 84 confirms whether the ID information which has been received by the transceiver 82 and which specifies the radiation converter 38 or the second image capturing apparatus 36 corresponds to the image capturing apparatus indicated by the image capturing order or not in step S7. If the ID information corresponds to the image capturing apparatus indicated by the image capturing order, then the controller 84 decides that the image capturing order does not need to be changed ("NO" in step S8), and selects the image capturing conditions for the first image capturing apparatus 34 or the second image capturing apparatus 36 from the image capturing condition storage unit 88 in step S9.

The selected image capturing conditions are sent from the controller 84 via the transceiver 82 to the radiation generator 44 of the first image capturing apparatus 34 or the radiation generator 50 of the second image capturing apparatus 36, and then set in the radiation source controller 78 of the radiation generator 44 or 50 in step S10. After the image capturing conditions are set in the radiation source controller 78 of the radiation generator 44 or 50, the radiological technician turns on the exposure switch 80 to apply the radiation emitted from the radiation source 76 to the subject 32. The radiation passes through the subject 32 to the radiation conversion panel 60 of the radiation converter 38 or the radiation conversion panel 46 housed in the image capturing base 48, whereupon a radiographic image of the subject 32 is captured in step S11. If the radiation is applied to the radiation conversion panel 60 of the radiation converter 38, the captured radiographic image is temporarily stored in the image memory 72.

The console 24 acquires the radiographic image from the first image capturing apparatus 34 or the second image capturing apparatus 36 in step S12. Then, the image processor 90 processes the radiographic image in step S13, and the processed radiographic image is displayed on the display unit 92 in step S14. The radiological technician confirms the radiographic image displayed on the display unit 92 and determines whether the radiographic image is acceptable or not, i.e., whether it needs to be recaptured or not, in step S15. If the radiographic image is not acceptable, i.e., it needs to be recaptured, then another radiographic image of the subject 32 is captured. If the radiographic image is acceptable, then it is sent via the in-house network 30 to the viewer 16 and displayed thereon so as to be interpreted by the doctor for diagnosis.

It is assumed that when the radiological technician is going to capture a radiographic image of the subject 32 using an image capturing unit placed in the image capturing room 20 according to the image capturing order for the subject 32, the image capturing room 20 has been occupied, and the radiological technician has decided to change from the image capturing room 20 to the image capturing room 18. In this case, the order storage unit 86 of the console 24 connected to the image capturing room 18 does not store the image capturing order for the subject 32. The console 24 requests and acquires the image capturing order for the subject 32 from the RIS 14, and cancels the image capturing order for the subject 32 which has been set in the console 26 connected to the image capturing room 20 in step S16. Thereafter, a radiographic image of the subject 32 is captured using the selected image capturing apparatus in the image capturing room 18.

It is also assumed that when the radiological technician is going to capture a radiographic image of the subject 32 using the second image capturing apparatus 36 in the image capturing room 18 according to the image capturing order for the subject 32, the subject 32 cannot take an upstanding posture due to a handicapped leg or the like. In this case, the radiological technician decides to change from the second image capturing apparatus 36 to the first image capturing apparatus 34 for capturing a radiographic image of the subject 32 while the subject 32 is lying on the image capturing base 42.

Then, the radiological technician prepares the first image capturing apparatus 34 for the capture of a radiographic image of the subject 32, and then turns on the power supply switch 70 of the radiation converter 38 to be used, generating an image capturing apparatus identification signal and sending ID information which identifies the radiation converter 38 to the console 24. The controller 84 of the console 24 confirms whether the transmitted ID information corresponds to the image capturing apparatus specified by the image capturing order or not. Since the ID information and the image capturing apparatus specified by the image capturing order do not correspond to each other in this case, the controller 84 changes the contents of the image capturing order in step S17, selects image capturing conditions with respect to the changed image capturing apparatus from the image capturing condition storage unit 88, and sets the selected image capturing conditions in the radiation generator 44 of the first image capturing apparatus 34. At this time, the radiological technician does not need to take the trouble of returning to the console 24 and resetting the image capturing unit specified by the image capturing order. It is assumed in this respect that though the radiological technician is unable to change the contents themselves of the image capturing order produced by the doctor, actual image capturing information, which is part of the image capturing order, indicating which image capturing unit has been used and what radiographic image has been captured, can be set as a change of the image capturing order made by the radiological technician, and can be recorded.

When the image capturing order is thus changed, the display unit 92 changes the present displayed contents of the image capturing order to the changed details, i.e., displays the changed details of the image capturing order.

When the first image capturing apparatus 34 is used to capture a radiographic image of the subject 32, the radiological technician may bring a radiation converter 38 that can be used from another image capturing room, and prepare the radiation converter 38 for the capture of a radiographic image of the subject 32. At this time, the radiological technician can automatically associate the introduced radiation converter 38 and the console 24 connected to the image capturing room 18 with each other by turning on the power supply switch 70 of the radiation converter 38.

As an image capturing apparatus selected by the radiological technician and a console which supplies appropriate image capturing conditions to the image capturing apparatus and processes an acquired radiographic image are properly associated with each other, as described above, the subject 32 as a patient is prevented from being mistaken and the image capturing conditions are prevented from being set in error, so that a desired radiographic image of the subject 32 can reliably be acquired.

Figure 5:
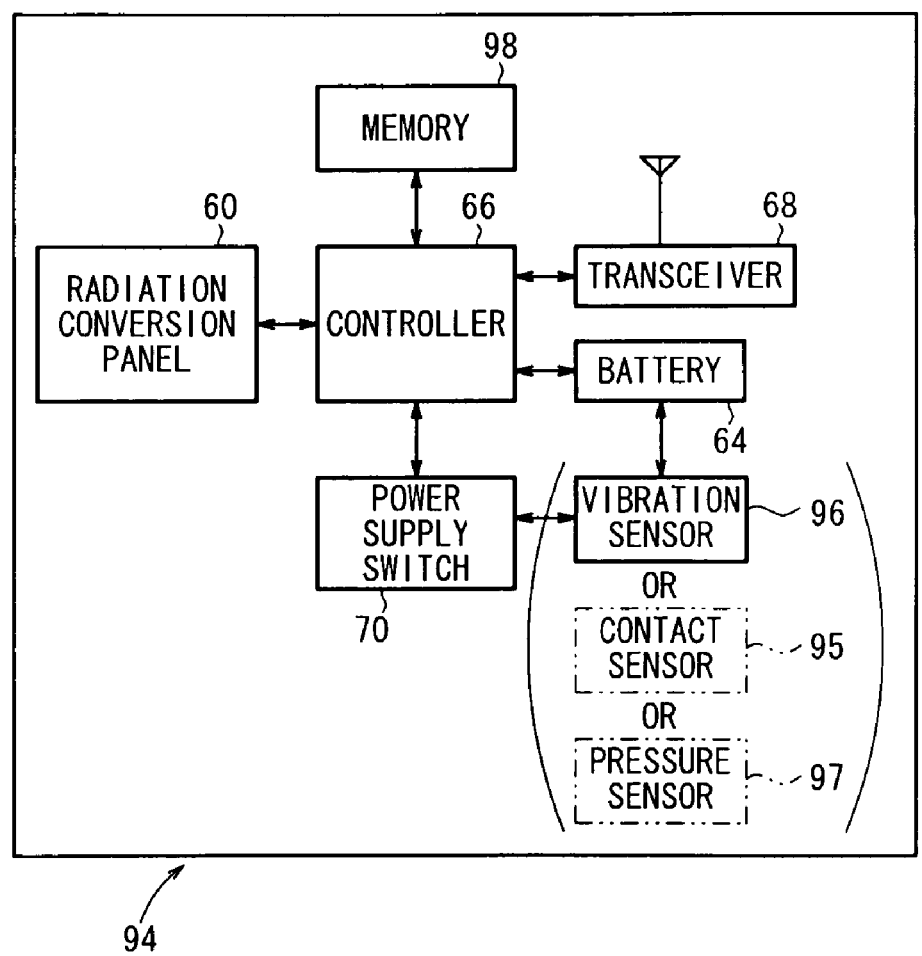
FIG. 5 is a block diagram of a radiation converter according to another embodiment of the present invention.

FIG. 5 shows in block form a radiation converter 94 according to another embodiment of the present invention. Those parts of the radiation converter 94 which are identical to those of the radiation converter 38 shown in FIG. 3 are denoted by identical reference characters, and will not be described in detail below.

As shown in FIG. 5, the radiation converter 94 includes a vibration sensor (identification signal generating unit) 96 for detecting vibrations of the radiation converter 94 produced when the radiation converter 94 is moved, and a memory 98 for storing a captured radiographic image as an electric signal.

The vibration sensor 96 detects vibrations at the time the radiological technician carries the radiation converter 94, thereby recognizing that the radiation converter 94 starts to prepare itself for the capture of a radiographic image of the subject 32. The controller 66 generates an image capturing apparatus identification signal based on the detected vibrations, and sends ID information specifying the radiation converter 94 to the console in the image capturing room. The console is now able to properly recognize that the radiation converter 94 to be used to capture a radiographic image of the subject 32 is selected by the radiological technician.

The radiation converter 94 may also include a contact sensor (identification signal generating unit) 95 for detecting a contact when the radiation converter 94 is contacted by the subject 32 or a pressure sensor (identification signal generating unit) 97 for detecting a pressure imposed on the radiation converter 94, thereby determining whether the radiation converter 94 is selected or not.

Figure 6:
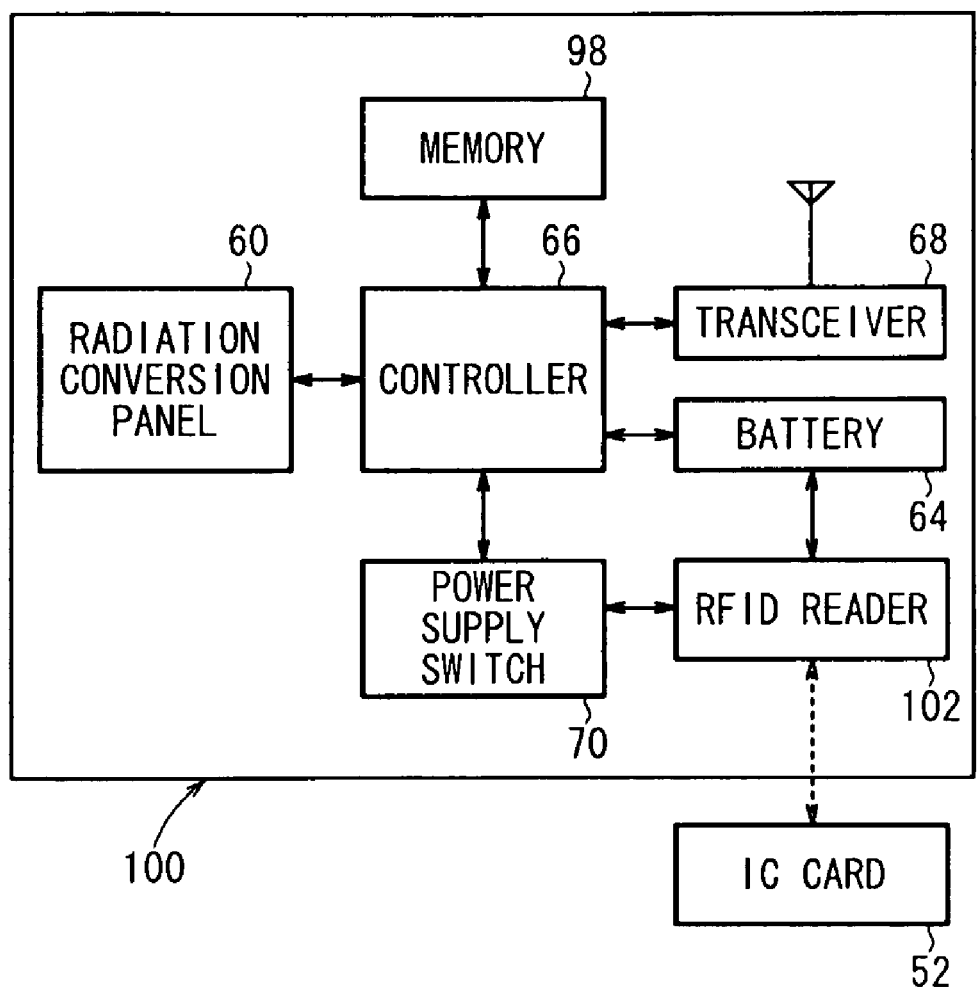
FIG. 6 is a block diagram of a radiation converter according to still another embodiment of the present invention.

FIG. 6 shows in block form a radiation converter 100 according to still another embodiment of the present invention. Those parts of the radiation converter 100 which are identical to those of the radiation converter 94 shown in FIG. 5 are denoted by identical reference characters, and will not be described in detail below.

As shown in FIG. 6, the radiation converter 100 includes an RFID reader (information reading unit) 102 for reading the IC card 52 which stores ID information of the subject 32 recorded therein. When the IC card 52 carried by the subject 32 is brought closely to the RFID reader 102, the radiation converter 100 is recognized to be used for capturing a radiographic image of the subject 32. The controller 66 generates an image capturing apparatus identification signal based on the recognition of the IC card 52, and sends ID information specifying the radiation converter 100 together with the ID information of the subject 32 read from the IC card 52 to the console in the image capturing room where the radiation converter 100 is placed, via the transceiver 68. The console is now able to properly recognize that the radiation converter 100 to be used to capture a radiographic image of the subject 32 is selected by the radiological technician. The console then supplies image capturing conditions depending on the characteristics of the radiation converter 100 to the radiation generator in the image capturing room. Based on the supplied image capturing conditions, the radiation generator generates and applies radiation to the subject 32, and the radiation converter 100 captures a desired radiographic image of the subject 32.

FIG. 7 shows in block form a radiographic image capturing system which incorporates a cassette 104 housing a stimulable phosphor panel IP therein according to yet another embodiment of the present invention.

As shown in FIG. 7, the cassette 104 includes an RFID reader 106 for reading the IC card 52 which stores ID information of the subject 32 recorded therein, a controller 108 for controlling the RFID reader 106, a transceiver 110 for sending the ID information read by the RFID reader 106 under the control of the controller 108, together with ID information specifying the cassette 104, to the console 24 by way of wireless communications, and a battery 112 for supplying electric power to the RFID reader 106, the controller 108, and the transceiver 110.

After the cassette 104 has prepared itself for the capture of a radiographic image of the subject 32, the IC card 52 is brought closely to the RFID reader 106, whereupon the controller 108 recognizes that the cassette 104 will be used to capture a radiographic image of the subject 32. The controller 108 generates an image capturing apparatus identification signal, and sends the image capturing apparatus identification signal together with the ID information specifying the cassette 104, via the transceiver 110 to a console 114 in the image capturing room where the cassette 104 is placed. The console 114 recognizes that the cassette 104 in the image capturing room is selected to capture a radiographic image of the subject 32, and supplies image capturing conditions depending on the characteristics of the stimulable phosphor panel IP in the cassette 104 to a radiation generator 116. Based on the supplied image capturing conditions, the radiation generator 116 generates and applies radiation to the subject 32, and the stimulable phosphor panel IP captures a desired radiographic image of the subject 32. The stimulable phosphor panel IP which has recorded the desired radiographic image of the subject 32 is supplied to a reading device 118, which reads the radiographic image.

The present invention is not limited to the various embodiments described above, but various changes and modifications may be made to the embodiments within the scope of the invention.

In the above embodiments, when the radiological technician turns on the power supply switch 70, or when the vibration sensor 96 detects vibrations when the radiological technician carries the radiation converter 94, or when the contact sensor 95 detects a touch to the radiation converter 94, or the pressure sensor 97 detects a pressure on the radiation converter 94, or when the RFID reader 102, 106 reads the IC card 52, the radiation converter 38, 94, 100 or the cassette 104 sends ID information, etc. to the console 24, 26, 28, 114, and then the image capturing apparatus as a unit except the console 24, 26, 28, 114 in the radiographic image capturing system 10, is selected, and the selected image capturing apparatus and the console 24, 114 are associated with each other.

Alternatively, when a power supply switch 200 (see FIG. 1) on the cradle 40, or an operating unit (power supply switch) 202 (see FIG. 1) on the image capturing base 42, or the exposure switch 80 (see FIG. 3), or an operating unit 204 (see FIG. 3, an exposure switch or a button on a display screen) on the radiation generator 50 is operated by the radiological technician, ID information, etc. may be sent to the console 24, 26, 28, 114, and the console 24, 26, 28, 114 may be associated with the image capturing apparatus related to the operating unit which has sent the ID information, etc. The operating unit (the power supply switch 200, the operating unit 202, the exposure switch 80, the operating unit 204) functions as an identification signal generating unit for generating an identification signal which identifies the image capturing apparatus selected by the radiological technician.

When the radiological technician operates one of the above operating units, the corresponding unit (the image capturing apparatus) except the console 24, 26, 28, 114 in the radiographic image capturing system 10 is selected, and the selected unit and the console are associated with each other.

When the radiological technician changes to an image capturing apparatus which is different from the one specified by an image capturing order and operates the operating unit related to the different image capturing apparatus, the console 24, 26, 28, 114 changes the contents of the current image capturing order to the contents of an image capturing order corresponding to the different image capturing apparatus, and the display unit 92 displays the details of the changed image capturing order.

Although certain preferred embodiments of the present invention have been shown and described in detail, it should be understood that various changes and modifications may be made therein without departing from the scope of the appended claims.

What is claimed is:

1. A radiographic image capturing system comprising:
    a plurality of image capturing units for capturing a radiographic image of a subject;
    a processor for supplying image capturing conditions to a selected one of the image capturing units and processing the radiographic image captured by the selected one of the image capturing units in a case where the selected one of the image capturing units is different from one of the image capturing units specified by an image capturing order for the subject;
    an identification signal generating unit for generating an identification signal which identifies the selected one of the image capturing units; and
    an associating unit for associating the selected one of the image capturing units with the processor according to the identification signal, and changing the image capturing order to correspond to the selected one of the image capturing units;
    wherein the image capturing conditions contained in the changed image capturing order are supplied from the associated processor to the selected one of the image capturing units that has been selected by a unit except the processor, and the radiographic image is supplied from the selected one of the image capturing units to the associated processor.

2. A radiographic image capturing system according to claim 1, wherein at least one of the image capturing units comprises:
    a radiation source for outputting radiation; and
    a radiation converter for converting the radiation which has passed through the subject into a radiographic image represented by an electric signal;
    wherein the radiation source is controlled according to the image capturing conditions depending on characteristics of the radiation converter.

3. A radiographic image capturing system according to claim 2, wherein at least one of the image capturing units includes an image capturing base which incorporates the radiation converter therein.

4. A radiographic image capturing system according to claim 1, wherein at least one of the image capturing units comprises:
    a radiation source for outputting radiation; and
    a stimulable phosphor panel for storing the radiation which has passed through the subject as a radiation energy;
    wherein the radiation source is controlled according to the image capturing conditions depending on characteristics of the stimulable phosphor panel.

5. A radiographic image capturing system according to claim 4, wherein at least one of the image capturing units includes an image capturing base which incorporates the stimulable phosphor panel therein.

6. A radiographic image capturing system according to claim 1, wherein the processor comprises a plurality of processors, and the associating unit associates the selected one of the image capturing units with a particular one of the processors.

7. A radiographic image capturing system according to claim 1, wherein the processor includes an image capturing condition holding unit for holding a plurality of sets of image capturing conditions corresponding respectively to the image capturing units, and the processor selects one of the sets of image capturing conditions which corresponds to the selected one of the image capturing units from the image capturing condition holding unit and supplies the selected one of the sets of image capturing conditions to the selected one of the image capturing units.

8. A radiographic image capturing system according to claim 1, wherein the processor includes an order holding unit for holding the image capturing order which specifies one of the image capturing units.

9. A radiographic image capturing system according to claim 1, wherein the identification signal generating unit comprises an operating unit on the selected one of the image capturing units.

10. A radiographic image capturing system according to claim 1, wherein the identification signal generating unit comprises a vibration sensor for detecting vibrations of the selected one of the image capturing units.

11. A radiographic image capturing system according to claim 1, wherein the identification signal generating unit comprises a contact sensor for detecting contact when the selected one of the image capturing units is contacted by the subject.

12. A radiographic image capturing system according to claim 1, wherein the identification signal generating unit comprises a pressure sensor for detecting a pressure imposed on the selected one of the image capturing units.

13. A radiographic image capturing system according to claim 1, wherein the identification signal generating unit comprises an information reading unit for reading information of the subject, the information reading unit belonging to the selected one of the image capturing units.

14. A radiographic image capturing system according to claim 1, wherein the image capturing units include a wireless transceiver unit for sending signals to and receiving signals from the processor by way of wireless communications.

* * * * *